United States Patent [19]

Gani et al.

[11] Patent Number: 5,910,462
[45] Date of Patent: Jun. 8, 1999

[54] ZIRCONIA PARTICLES

[76] Inventors: Mary Susan Jean Gani, 27 Stockdale Avenue, Clayton North, Victoria 3168, Australia; Hans-Jurgen Wirth, 6 Baringa Ave., Kallista, Victoria 3791, Australia; Marie Isabel Aguilar, Lot 21, Glynns Road, Warrandyte, Victoria 3113, Australia; Milton Thomas William Hearn, 263 Union Road, Balwyn, Victoria 3103, Australia; Donald George Vanselow, 54 Greenways Road, Glen Waverley, Victoria 3150, Australia; Philip Hong Ning Cheang, Nanyang Technological University, School of Applied Science, Division of Materials Engineering, Nanyang Avenue, Singapore, Singapore; Kjell-Ove Eriksson, P.O. Box 278 (Hickory Hills Dr. 49), Bath, Pa. 18014

[21] Appl. No.: 08/591,609
[22] PCT Filed: Jul. 28, 1994
[86] PCT No.: PCT/AU94/00425
   § 371 Date: Jun. 4, 1996
   § 102(e) Date: Jun. 4, 1996
[87] PCT Pub. No.: WO95/04012
   PCT Pub. Date: Feb. 9, 1995

[30]   Foreign Application Priority Data

Jul. 28, 1993 [AU] Australia ............................... PM 0247
Jul. 28, 1993 [AU] Australia ............................... PM 0248

[51] Int. Cl.⁶ ..................... C04B 35/48; C04B 35/653; C04B 38/04
[52] U.S. Cl. ........................... 501/80; 501/103; 264/42; 264/43
[58] Field of Search ..................... 501/80, 103; 264/42, 264/43

[56]   References Cited

U.S. PATENT DOCUMENTS 3,421,914  1/1969  Hare ............................................. 501/80
3,892,580  7/1975  Messing ....................................... 501/80

(List continued on next page.)

FOREIGN PATENT DOCUMENTS 3009992  7/1993  Australia .
 216730  4/1987  European Pat. Off. .

(List continued on next page.)

OTHER PUBLICATIONS

Journal of the American Ceramic Society, 68[12], 1985 (Westerville, Ohio) Tsugio, Stao, et al, Transformation of Yittria–Diped Tetragonal $ZrO_2$ Polycrystals by Annealing under Controlled Humidity Conditions:, pp. c–320–c–322. No month.

(List continued on next page.)

Primary Examiner—Mark L. Bell
Assistant Examiner—David Sample
Attorney, Agent, or Firm—Biebel & French

[57]   ABSTRACT

Porous zirconia or zirconium-containing particles, methods of making such particles and methods of using such particles including modifications to the surface of the particles are described. The method comprises heating zirconia particles to provide a substantially homogeneously liquid melt, quenching the particles of melt to effect spinodal decomposition to provide quench particles of a silica rich phase and a zirconia rich phase, annealing the quenched particles to provide non porous solid particles of zirconia and silica and, leaching the silica from these particles to produce porous solid zirconia particles comprising a three dimensionally substantially continuous inter penetrating network of interconnected pores.

49 Claims, 7 Drawing Sheets

U.S. PATENT DOCUMENTS

| | | | |
|---|---|---|---|
| 4,203,772 | 5/1980 | Davis, Jr. et al. | 501/80 |
| 4,735,922 | 4/1988 | Ray | 501/80 |
| 4,888,309 | 12/1989 | Araya | 501/80 |
| 4,923,830 | 5/1990 | Everhart et al. | 501/103 |
| 5,023,217 | 6/1991 | Everhart et al. | 501/103 |
| 5,384,290 | 1/1995 | Brezny | 501/81 |
| 5,399,535 | 3/1995 | Whitman | 501/80 |
| 5,563,106 | 10/1996 | Binner et al. | 501/84 |

FOREIGN PATENT DOCUMENTS

| | | |
|---|---|---|
| 295073 | 12/1988 | European Pat. Off. . |
| 331283 | 9/1989 | European Pat. Off. . |
| 501142 | 9/1992 | European Pat. Off. . |
| 2153807 | 8/1985 | United Kingdom . |
| 8504158 | 9/1985 | WIPO . |
| 8707915 | 12/1987 | WIPO . |

OTHER PUBLICATIONS

Verre, 1987, 1(5), (Paris), Johnson, PJ, et al, "Glass Ceramic rich in Lanthanum oxide ($La_2O_3$)–Zirconium dioxide with interconnected pores", pp. 565–570. No month.

South African Journal of Physics, 8, (3), 1985 (Pretoria), Hart, S, et al, "$ZrO_2$–rich glass ceramic with interconnected pores", pp. 50–55. No month.

Derwent Abstract Accession No. 89–097552, Class S03, Jp, A, 01–046646 (Shimadzu Seisakusho KK) Feb. 21, 1989 (abstract).

Journal of the American Ceramic Society, 69[7], 1986 (Westerville, Ohio) Robert R. Hughan and Richard H.J. Hannink, "Precipitation During Controlled Cooling of Mangesia–Partially–Stabilized Zirconia", pp. 556–563. No month.

Journal of the American Ceramic Society, 70[10], 1987 (Westerville, Ohio) A.H. Heuer, "Transformation Toughening in $ZrO_2$–Containing Ceramics", pp. 689–698. No month.

ZIRCONIA PARTICLES

INTRODUCTION

The present invention relates, generally, to porous articles, and in particular to porous zirconia or zirconium containing articles, to methods of making such articles, and to methods of using such articles. One example of the porous articles are porous particles. More particularly, the present invention relates to porous particles containing zirconia and other metallic oxides including silica in combination and to the manufacture and use of such particles. Even more particularly, the present invention relates to the use of particles containing zirconia and other metallic oxides including optionally containing silica, in separation applications, particularly in chromatographic applications. One particular aspect of the present invention relates to derivatisation processes whereby the surface of the porous zirconia or zirconium containing particles are modified and to the use of such modified particles in chemical processes, particularly in chromatographic applications.

Porous articles find use in certain applications because of their properties, such as for example, their high surface area per unit volume. Such uses include use as supports for a wide variety of chemical substances, such as catalyst supports and as chemical sorbents. Where the porosity and the pore size of the particles can be controlled, the porous particles also find particular use in chromatography applications and in chemical separation applications generally. Porous silica, one example of a porous particle, finds particular use in chromatographic applications, such as High Performance Liquid Chromatography (HPLC). However, the use of porous silica is limited by the chemical reactivity of the particles since porous silica is susceptible to reactions in alkaline media and therefore is of only limited use in applications which require resistance to alkaline attack or for operations conducted in alkaline media. Thus, there is a need for a porous material which is not susceptible to alkaline attack and can be used in alkaline media.

Another example of porous articles are organic polymers which are particularly useful in a wide variety of applications due to their pore size or to the pore sizes being readily controllable. However, at high temperatures and in certain organic solvents, or when subjected to certain mechanical stress, the organic polymers have limited strength, and can distort altering their pore sizes which in turn changes the separation characteristics of the polymers and thus reduces their effectiveness and usefulness in many applications. Disadvantages of using polymers are particularly prevalent in situations where the polymer particles are mixed with liquids, since the low density of the organic polymer particles, being similar to that of the liquids, prevents their ready separation from the liquid. In particular, low density polymeric particles are difficult to handle in fluidised beds due to the similarities of the densities of the particles and of the liquids being treated in the fluidised bed. Thus, there is a need to provide porous particles which retain their shape in a wide variety of chemical and mechanical environments in order to prolong the useful working life of the particles and to increase the variety of applications in which the particles may be used. Additionally, there is a need to provide porous particles which can be readily separated from the liquids being treated by the particles on the basis of the difference in densities of the particles and liquids.

In the past there has been a proposal to use porous zirconia particles as the support phase for chromatography applications (Rigney, Webber and Carr, Journal of Chromatography 484 (1989) 273–291). However, this proposal was not entirely successful due to the particles being unstable in some mechanical environments encountered in chromatographic applications and due to the inability to modify the surface properties of the particles. Such disadvantages arose primarily from the method used in making the particles. The present invention sets out to overcome these and other weaknesses of the particles and of the previously used method of making the particles.

Therefore, there is a need for porous particles which are resistant to alkaline attack, which are of improved strength and of high density, which can be used in a wide variety of chemical separation applications and which extend the applications in which such porous particles can be utilised by modifying the surface of the particles. It has now been discovered that it is possible to make porous is zirconia which can provide improved resistance to alkaline attack, which is of good strength and has a relatively high density and which can be used in diverse chemical and mechanical environments in which hithertobefore it has not been possible to use porous zirconia particles. The improved properties result at least in part from the method of making the particles.

Porous Zirconia Particles

According to one aspect of the present invention there is provided porous zirconia particles or zirconium-containing particles in which the particles comprise a substantially continuous three dimensional interpenetrating network of interconnected pores.

Typically, the pores of the particles are of substantially constant diameter throughout their length. More typically, the pores have substantially constant diameter at the curves or bends of the pores, and at the intersection of the pores. However, it is to be noted that where two or more pores intersect, the diameter of the pores may be changed to account for the individual pores not being exactly aligned with each other.

Typically, the zirconia or zirconium-containing particles also comprise a further component. Typically, this component is a metal oxide, such as for example silica. More typically, the particles of the present invention comprise a combination of zirconia and silica and can optionally include zircon. Preferably, there is from 1 to 100% zirconia and from 99 to 0% silica, more preferably 5–90% zirconia and 95–10% silica.

Typically, the size of the particles can be up to 200 µm or greater, preferably 5–100 µm, more preferably 5 to 80 µm and even more preferably 10–70 µm.

Preferably, the porous zirconia of the present invention comprises particles having interconnected pores of up to about 2000 Å or greater, preferably between about 20 and 2000 Å in diameter, more preferably between 200 and 1500 Å in diameter, and even more preferably, pores of between 500 and 1000 Å in diameter. However, it is to be noted that pores of up to 5000 Å or even larger are possible with some of the particles of the present invention depending on the size of the particles. When the pore sizes become too large the effectiveness of the particles in chemical separation applications reduces because the surface area of the particles is reduced.

Typically, the surface area per unit mass of the particles can be up to 100 $m^2/g$, preferably 5 to 30 $m^2/g$ with a typical value being about 5 $m^2/g$.

Typically, the surfaces of the porous zirconia particles may be modified, more typically, the outer surfaces of the particles or surfaces of the pores closer to the outer surface of the particles. More typically, the surface modification of the particles involves hydroxylation of the surface to impart a greater amount of hydroxide groups on the surface of the particles.

Even more typically, the surface modified or surface treated particles can be further modified with other functional groups. The surface modified particles find particular usefulness in chromatography applications.

It will be understood that by use of the term "zirconia" in the present specification is meant zirconia-rich compositions such as those commonly referred to in the art as zirconia compositions or compositions containing a significant proportion of zirconia or zirconium, preferably at least about 50% zirconia.

Crystallographic forms of Zirconia

Zirconia, which is also known as zirconium oxide ($ZrO_2$), may exist at room temperature in any of three crystallographic forms; monoclinic, tetragonal or cubic. The monoclinic form is the most stable at room temperature, which is to say that this crystallographic form has the lowest bulk energy of all three forms at this temperature. The tetragonal form is of higher energy than the monoclinic form and can be stabilised at room temperatures by the addition of dopants such as for example, rare earth oxides including yttria, and also calcia and magnesia. Preferably, the tetragonal form may be stabilised at room temperatures by the inclusion of yttria or other rare earth oxides depending upon the grain size of the crystallites of tetragonal zirconia, amongst other factors.

The transformation of zirconia from the tetragonal to monoclinic form is accompanied by a 4% volume increase. Below a critical grain size, which will be dependent on a number of factors, including the nature of the matrix material in which the zirconia is embedded, the tetragonal form will be metastable due to the fact that the increase in surface energy which would accompany a 4% volume increase is greater than the reduction in the bulk energy on the transformation from the tetragonal to monoclinic form.

The cubic form which is of the highest bulk energy is more unstable at room temperatures than the other forms, and may be stabilised at these temperatures by the addition of dopants such as calcia and magnesia.

The crystallographic form of the zirconia present in particular particles may be readily determined by any number of known methods, including X-ray diffraction.

It is to be noted that the porous zirconia particles or zirconia-containing particles of the present invention may take any crystallographic form or combination of forms of the zirconia.

It has been found that the monoclinic form of the zirconia is the preferred crystallographic form from which the porous zirconia particles of the present invention can be composed and results in particles having the most desired properties for porous materials used in chemical separation applications. Therefore, it is preferable to use starting materials which produce porous monoclinic zirconia particles comprising the substantially continuous three dimentionally interpenetrating network of interconnected pores.

Further it is to be noted that where it is desired to surface modify the porous zirconia particles, it is not at all critical that the porous particles are composed of the monoclinic form of zirconia. The porous monoclinic zirconia particles of the present invention exhibit improved strength and increased density when compared to conventional porous materials such as porous silica or porous organic polymers. Therefore, the porous monoclinic zirconia is particularly useful in applications for the separation of chemicals and biochemicals, particularly using chromatographic or biochromatographic techniques and other techniques such as batch procedures using stirred tanks, batch tanks, fluidised beds and the like.

The preparation of porous monoclinic zirconia having the required properties requires careful control of the crystallographic structure and of the morphology of the zirconia. Therefore, another aspect of the present invention relates to a process for the production of porous monoclinic zirconia.

Method of Making Porous Monoclinic Zirconia

According to the present invention there is provided a method for the production of porous monoclinic zirconia comprising the following steps in sequence:

(a) heating a zirconia-silica composition to provide particles of said composition in the form of a substantially homogeneous liquid melt;

(b) quenching said particles to effect spinodal decomposition of the liquid melt to provide quenched solid, non-porous particles comprising a silica-rich phase and a zirconia-rich phase, wherein the zirconia-rich phase comprises zirconia substantially in tetragonal form;

(c) annealing said quenched particles to transform the tetragonal form of the zirconia-rich phase to the monoclinic form on cooling so as to provide annealed particles comprising a continuous monoclinic zircornia-rich phase and a continuous silica-rich phase;

(d) leaching said silica-rich phase from the annealed particles to provide porous monoclinic zirconia comprising a three dimensionally substantially continuous interpenetrating network of interconnected pores.

In the process for producing porous monoclinic zirconia particles according to the present invention, a zirconia-silica composition is used as the starting composition, which zirconia-silica composition is heated to form the homogeneous liquid melt which undergoes phase separation on cooling to form one phase of zirconia and another of silica.

Typically, in step (c) a third phase is formed. This third phase is typically zircon. More typically, the zircon phase is not leached away when the silica phase is being leached. Even more typically, the porous particles contain zircon in addition to the zirconia.

The zirconia-silica composition used in step (a) may be either an admixture of zirconia or a zirconia-containing material and silica or a silica-containing material or may be a compound containing both zirconium or zirconia and silica or combination thereof. Additionally, compositions or compounds which decomposes to provide a homogeneous liquid melt of zirconia and silica may be used.

Preferably, the starting material used in this method of the present invention is commercially available zircon. More preferably the zircon undergoes a pretreatment such as for example sieving or similar to suit the end uses to which the porous particles are to be put. Typically, the commercial zircon is screened to remove coarse particles greater than 100 $\mu$m.

Typically, the zirconia:silica volume ratio in the quenched particles is about 1:1. This ratio provides porous monoclinic zirconia after leaching of a particularly uniform structure and of substantially even porosity. The molar volumes of both silica and zirconia are very similar to each other and hence it is desirous to select a zirconia-silica composition wherein the molar ratio of zirconia to silica is about 1:1, in order to achieve a volume ratio of about 1:1. Where the zirconia-silica composition used in this form of the method of the present invention is a composition which decomposes to a homogeneous liquid melt of zirconia and silica the composition should decompose to give a mixture of zirconia and silica in a molar ratio of about 1:1. However, it is to be noted that the ratio of zirconia to silica can be altered according to the final properties required of the porous particles since the leaching of the silica is responsible for the productions of pores in the zirconia particles and hence the amount of silica originally present in the starting zirconia-silica composition determines at least in part the amount of the pores present in the particles.

Typically, zircon is a particularly preferred form of the starting zirconia-silica composition. Zircon has the molecular formula $ZrSiO_4$ and decomposes to a 1:1 molar mixture of zirconia ($ZrO_2$) and silica ($SiO_2$).

Typically, admixtures of zirconia and silica or materials containing these compounds may also be conveniently used to provide a volume ratio of about 1:1. However, it is to be noted that any ratio may be used. Admixtures may also be used to provide varying volume ratios, thereby allowing the degree or amount of porosity to be controlled in the porous zirconia.

Typically, the pore size of a single particle is substantially constant. However, the pore sizes may vary between particles. A typical pore size distribution can be from 0.01 to 0.2 $\mu$m for a particle size range of from 40 to 80 $\mu$m.

Typically, the zirconia-silica composition may conveniently be provided in the form of a powder or particles. The size of the particles will be determined by a number of factors. The zirconia-silica particles are desirably of a size conveniently adapted for the end use of the porous zirconia in the desired application, such as, for example, use as chromatographic powders and the like. The zirconia-silica particles are preferably sufficiently small so as to be able to form a homogeneous liquid melt. This size will be determined by such things as the heating rate, heating time and thermal conductivity of the zirconia-silica particles amongst other factors. The zirconia-silica particles should also be sufficiently small so as to allow the homogeneous liquid melt to be quenched at a rate which allows spinodal decomposition of the liquid melt as will be discussed in more detail later in this specification. This size will be determined by the required cooling rate which itself is dependent on the composition of the zirconia-silica composition, the temperature of the quenching medium, the efficiency of heat transfer from the particles to the quenching medium and the thermal conductivity of the particles among other factors.

Typically, the zirconia-silica composition should ideally be heated to provide a homogeneous liquid melt. The temperature necessary will be dependent on the zirconia-silica composition. For example, the zirconia-silica composition which is equivalent to that of zircon forms a liquid at temperatures in excess of about 2400° C. Typically, the zirconia-silica composition would be heated to temperatures well above their respective melting temperatures so that the time for forming the homogeneous liquid melt is reduced.

Typically, the zirconia-silica composition may be heated in any convenient heating apparatus available to the skilled artisan, which heating apparatus is capable of producing temperatures sufficiently high to melt the zirconia-silica composition. It has been found particularly preferable to utilise a plasma arc torch or reactor to heat the zirconia-silica composition. When using a plasma arc reactor the zirconia-silica composition is preferably in the form of particles comprising an intimate mixture of zirconia and silica or in the form of a composition which will decompose to form an intimate mixture of silica and zirconia. Zircon may be conveniently used as one example of the zirconia-silica composition in a plasma arc torch. The particularly preferred particles of zircon for use in a plasma arc torch have a particle size in the range of from 5 $\mu$m to 100 $\mu$m in size.

More preferably, the zircon particles are in the range of 10 to 55 $\mu$m. Typically, the zircon particles are elongated, or acicular and on heating the particles first disassociate and then melt to form a homogeneous liquid melt.

Typically, the use of smaller zirconia-silica particles allows the use of lower temperatures for heating, such as for example, passing through an oxyacetylene or oxyhydrogen flame. Typical particle sizes useful with flame spraying are in the range of from 3 to 15 $\mu$m.

Typically, the particles of the homogeneous liquid melt are quenched at a cooling rate sufficient to prevent nucleation and growth of zirconia spherulites and to allow spinodal decomposition of the liquid melt into zirconia-rich and silica-rich phases. The spinodal decomposition of the homogeneous liquid melt gives an extremely fine microstructure of zirconia-rich and silica-rich interpenetrating networks which exhibit uniform periodicity and three dimensional continuity.

Typically, the quenched solid, non-porous particles have wave lengths of approximately 100 Å between the different phases. By "wave length" in the present specification is meant the average distance between one phase and the next.

By the term "uniform periodicity" is meant the wave length is substantially uniform.

By the term "three dimensional continuity" is meant that each phase forms an interconnected three dimensional network.

Typically, the spheroidal particles formed from the homogeneous liquid melt are quenched in a water bath. However, other liquid quenching media may be used. Liquid quenching media are preferred due to the high heat transfer rates which can be achieved between the particles and the; liquid.

Typically, quenching will provide a cooling rate of the order of about $10^5$ to $10^7$ °C. sec$^{-1}$. However, other quenching rates are possible.

It will be understood by those skilled in the art that by the term "zirconia-rich" is meant a phase containing a higher percentage of zirconia than contained in the original homogenous liquid melt of the zirconia-silica composition.

It will be understood by those skilled in the art that by the term "silica-rich" is meant a phase containing a higher percentage of silica than in the original homogeneous liquid melt of the zirconia-silica composition.

Typically, the quenched particles comprise both a zirconia-rich and a silica-rich phase. The zirconia-rich phase will be substantially in the tetragonal form which is metastable and on leaching of the silica-rich phase therefrom will transform to the stable monoclinic form. This transformation is accompanied by a 4% volume increase which generally leads to the disintegration of the zirconia-rich network. Therefore, if it were not for the annealing stage prior to the leaching stage it would not be possible to produce porous particles having the characteristics and properties possessed by the particles of the present invention.

The quenched particles are therefore annealed to coarsen the zirconia-rich phase. Typically, the annealing takes place below the temperature at which substantial recombination of zirconia and silica occurs at an appreciable rate. This temperature will be dependent on the composition of the zircona-rich phase and be readily determinable by simple experimentation by the skilled artisan. However, it is to be noted that it is preferable for some recombination of the silica and zirconia to take place to form zircon of a similar structure to enhance the strength of the porous particles produced by leaching the uncombined silica therefrom.

Preferably, the annealing takes place at a temperature sufficient for the coarsening of the zirconia-rich phase at a rate convenient for manufacture, which is to say at a rate which is fast enough to be accomplished on a reasonable time scale, but not so fast as to render the coarsening uncontrollable. Preferably, the annealing takes place at a temperature in the range of from about 1000° C. to 1400° C., preferably 1200° C. to 1400° C. and is achieved over a period of up to 5 hours, preferably from about 1 to 5 hours depending on the particle size of the particles.

Typically, the degree of coarsening of the zirconia-rich matrix aids in determining the pore size in the porous zirconia. The longer or more extensive the coarsening the larger the pore size in the porous zirconia. Typically, the coarsening of the zirconia-rich phase occurs by diffusion of zirconia and silica. During coarsening, the grain size of the zirconia crystallites increases. Typically, the zirconia is of a grain size sufficient to allow the zirconia to transform from the tetragonal form to the monoclinic form on cooling to ambient temperature. The critical grain size is dependent on the composition of the zirconia-rich phase. The temperature of the transformation from the tetragonal to monoclinic form is dependent on the composition of the zirconia-rich phase and the grain size of the zirconia crystallites. However, it is to be noted that it is preferable to have some silica or zircon present in the zirconia phase before leaching to prevent collapse of the substantially pure zirconia particles.

The transformation temperature of dissociated zircon that has been quenched and subsequently annealed is typically about 720° C. After the quenched particles have been annealed it is preferred that the particles are cooled slowly through the transformation temperature so as to avoid disintegration of the particles so that particles having improved strength can be obtained.

It is preferred that the zirconia-rich phase is not coarsened to such an extent that the transformation of the tetragonal form to the monoclinic form, with its accompanying 4% volume increase, leads to shattering of the annealed particles on cooling. Above a critical size, determined by the composition of the silica-rich phase among other factors, the zirconia-rich phase on transformation introduces strains into the silica-rich phase which can cause it to fail on cooling.

The annealed particles are then leached to remove the silica-rich phase. Alkali or hydrofluoric acid may be used to leach the silica-rich phase. Preferably, the annealed particles are leached with alkali, more preferably with sodium hydroxide. Typically, the rate of leaching is increased with increased temperature. More preferably, the annealed particles are leached with sodium hydroxide at a temperature of about 160° C.

Method of Making Porous Tetragonal Zirconia

According to another aspect of the present invention there is provided a process for the production of porous tetragonal zirconia comprising the following steps in sequence:
(a) heating a zirconia-silica composition to provide particles of said composition in the form of a substantially homogeneous liquid melt;
(b) quenching said particles to effect spinodal decomposition of the liquid melt to provide quenched particles comprising a silica-rich phase and a zirconia-rich phase;
(c) annealing said quenched particles to coarsen the zirconia-rich phase so that the desired pore diameter can be obtained after step (d); and
(d) leaching said silica-rich phase from the annealed particles to provide porous tetragonal zirconia comprising a three dimensionally continuous interpenetrating network of interconnected pores.

Preferably, the tetragonal zirconia is stabilised by the addition of dopants, such as for example, rare earth oxides including yttria, calcia or magnesia or combinations thereof. More preferably, yttria is used as the dopant. In order to produce porous tetragonal zirconia it is preferred that the dopants are intimately incorporated into the zirconia-silica composition in the initial heating step. This enables a homogeneous liquid melt to be readily formed on heating.

Typically, the zirconia-silica composition further comprises a dopant. Typically, the dopant is a rare earth oxide, preferably yttria. Typically, the dopant exists as particles in the zirconia-silica composition. More typically, two phases are formed in step (b), the dopant being preferably incorporated into the zirconia-rich phase.

The process for producing porous tetragonal zirconia as hereinabove described may be carried out according to the parameters described with reference to the process for producing porous monoclinic zirconia except for the annealing step. The annealing step in the process for producing porous tetragonal zirconia preferably produces grains of tetragonal zirconia which are stabilised by the presence of the dopant with respect to transformation to the monoclinic form on cooling to ambient temperature and throughout the leaching process. The stability of the grains of tetragonal zirconia is dependent on the composition and amount of dopants in the zirconia-rich phase among other factors.

Porous tetragonal zirconia is particularly strong and can provide particles which are particularly useful due to their strong and robust nature.

Method of Making Cubic zirconia

According to another aspect of the present invention there is provided a process for the production of porous cubic zirconia comprising the following steps in sequence:
(a) heating a zirconia-silica composition to provide particles of said composition in the form of a substantially homogeneous liquid melt;
(b) quenching said particles to effect spinodal decomposition of the liquid melt to provide quenched solid, non-porous particles comprising a silica-rich phase and a zirconia-rich phase;
(c) annealing said quenched particles to coarsen the zirconia-rich phase so that the desired pore diameter can be obtained after step (d); and
(d) leaching said silica-rich phase from the annealed particles to provide porous cubic zirconia comprising a three dimensionally continuous interpenetrating network of pores.

Preferably, the cubic zirconia is stabilised by the addition of dopants, such as, for example, calcia, magnesia and the like. Typically, the dopant must be present in sufficient quantities to stabilise the cubic form of the zirconia. In order to produce porous cubic zirconia it is preferred that the dopants are intimately incorporated into the zirconia-silica composition. This enables a. homogeneous liquid melt to be readily formed on heating.

The process for producing porous cubic zirconia as hereinabove described may be carried out according to the parameters described with reference to the process for producing porous monoclinic zirconia except for the annealing step. The annealing step in the process for producing porous cubic zirconia preferably produces grains of cubic zirconia which are stabilised with respect to transformation to either the tetragonal or subsequently monoclinic form on cooling to ambient temperature and throughout the leaching process. It is to be noted that while the annealing step is not necessary to stabilise the zirconia particles, it influences the pore size of the particles. The stability of the grains of cubic zirconia is dependent on the composition and amount of dopants in the zirconia-rich phase as well as the grain size among other factors.

Derivatised Porous Zirconia

It is a further object of the present invention to provide derivatised porous zirconia particles with enhanced stability under alkaline conditions, with enhanced strength in a wider variety of harsh environments so that such particles can be used in a wider variety of chemical separation applications, and with a wide variety of functional groups on the surface of the particles so that the porous particles can be used in a wide variety of chemical separation processes, including chromatographic applications.

According to the present invention there is provided porous zirconia particles having functional molecules attached to the surface of the particles via a silane group reacting with surface hydroxyls on the particle surface of the zirconia particles.

In a further form of the present invention there is provided porous zirconia particles having a shell of organic polymer around or surrounding the zirconia particles wherein the polymeric shell is cross-linked and attached to the hydroxyl groups on the surface via silanes.

The present invention also relates to a method of preparing derivatised porous zirconia particles by first treating the particles via a hydrothermal process to increase the hydroxyl group density on the particle surface, and then reacting the hydroxyl surface group with a silane.

Silane is a term recognised in the art relating to silicon hydrides and includes disilanes as well as trisilanes. Other chemical groups may be coupled to the silane molecules.

The hydrothermal treatment as practised in accordance with the present invention is used to reintroduce hydroxyl groups to the surface of a zirconia particle and to provide a high and uniform hydroxyl group density on the surface. The hydrothermal treatment is performed at temperatures between 100 and 300° C., typically 150° C. and elevated pressures. The pressure inside the autoclave is due to vapour pressure of water and is a function of the temperature of the autoclave.

A high and uniform hydroxyl group density is a requirement for a high ligand density during subsequent modification of the surface properties of the zirconia particle. The quality of the modification and therefore the effectiveness of the hydrothermal treatment is measured indirectly by determination of the uncovered zirconia surface area. The effectiveness of the hydrothermal treatment is dependent on the duration of the treatment and the temperature (pressure) involved. The higher the temperature the faster the kinetics. As an example, using a temperature of 150° C. the optimum reaction time for the hydrothermal treatment of the zirconia particles is 6 hours. However, any temperature, time, pressure combination within the limits of each of these parameters can be used in the hydrothermal treatment to hydroxylate the surface of the particles.

In a further embodiment the invention provides a method of preparing derivatised porous zirconia particles with a polymeric shell on the surface by adsorbing a monomeric material onto the surface and then polymerising the monomeric material to form the polymeric shell.

The porous zirconia of the present invention may be derivatised by the attachment of organic molecules to the surface of the porous zirconia. Such organic molecules which may be attached to the surface of the porous zirconia include affinity dyes, hydrophobic and hydrophilic surfaces and the like, one example of which are the silanes. Typically, the surface of the porous zirconia particles is activated with a substituted silane onto which the organic molecule is bound. The derivatisation of the porous zirconia provides an increased range of separation applications for which the porous zirconia may be used and thus extends the application of the present invention.

It is to be noted that the porous zirconia or zirconia-containing or zirconium containing particles, optionally containing other metallic oxides, such as rare earth oxides and including silica, may be modified by attaching any suitable, desirable or convenient chemical groups or molecules onto the surface depending on the properties desired of the particles and the applications in which the particles are to be used.

Examples of chemical groups or molecules that can be attached to the particles, including the following: Hydrophobic ligands in the form of alkyl chains, aromates or cyano groups, hydrophilic ligands like polyols, carbohydrates, polyethers or polyesters, anionic and cationic ion exchangers over a wide range of ionic strength, peptides, proteins, enzymes, metal chelates and molecules forming specific interactions with biological active substances, lipids, DNA, RNA, dyes oligonucleotides, and the like. It is to be noted that the foregoing list is not exhaustive but rather is merely illustrative, as would be apparent to the skilled worker.

It will be evident to those skilled in the art that the list is not exclusive.

Another embodiment of the present invention relates to the use of porous particles in a process of chromatographically separating proteaceous molecules.

The invention will now be described by way of example with reference to the accompanying drawings and the following non-limiting examples in which:

IN THE DRAWINGS

EXAMPLE 1

Manufacture of Monoclinic Zirconia Particles

Figure 1:
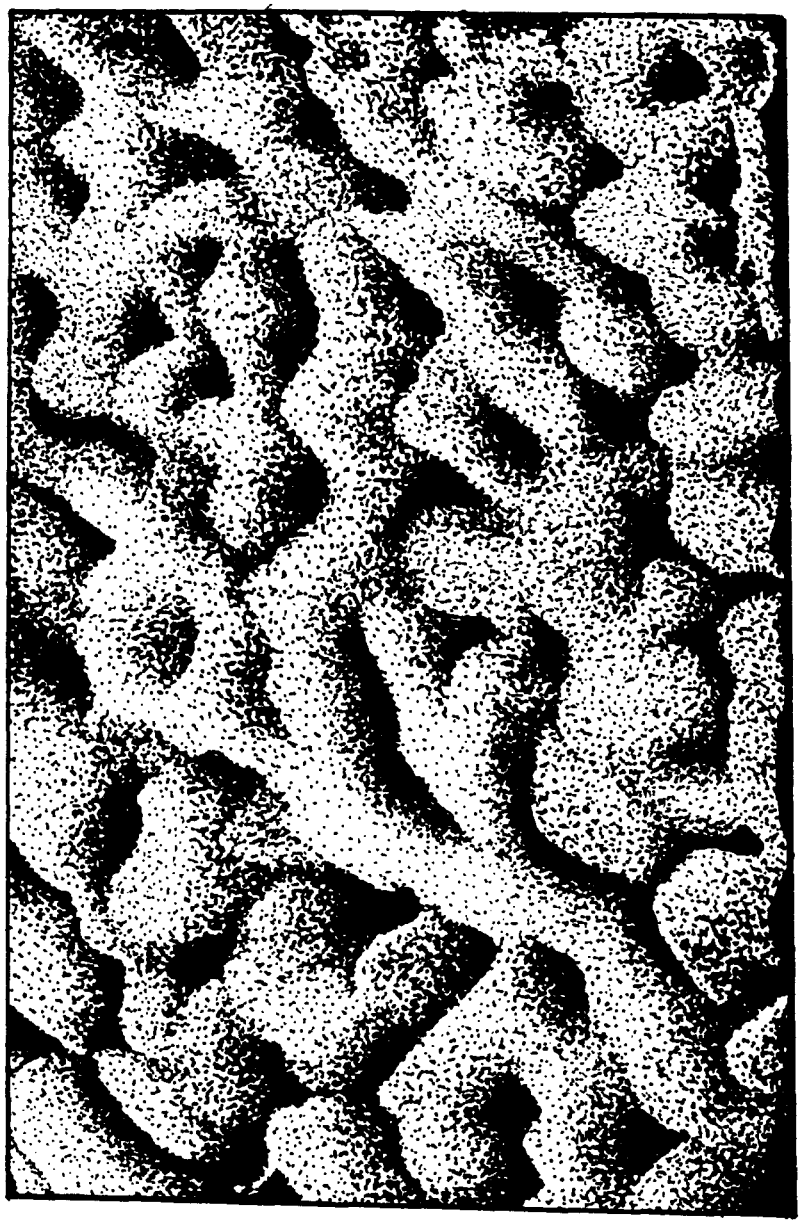
FIG. 1 is a high magnification photo-micrograph of a caustic leached annealed particle of zirconia showing the interconnected pore structure in accordance with the present invention.

Zircon flour (supplied by Commercial Minerals) was first sifted to remove particles coarser than ~50 μm and then flame sprayed in order to improve the flow characteristics of the powder such as by rounding or smoothing of the particles' surfaces. The flame spraying was carried out in a Metco Type 6P-II Thermospray Gun flame spraying torch, specifically designed for the flame spraying of ceramic and metallic powders. The powders were injected into an oxy-acetylene flame with the assistance of a Metco Type 4PM Powder feed unit. The oxy-acetylene flame being slightly oxidising, this resulted in the finer (<~10 μm diameter) particles being spheroidised. It is to be noted that the flame temperature was not sufficiently high to melt and spheroidise the larger particles. This step was found to be necessary in some circumstances as it was found to be difficult to introduce the untreated powder directly into the plasma torch on occasions. The flame sprayed powder was collected in distilled water. After the powder had been dried, it was then plasma sprayed, and again collected in distilled water. The powder was plasma sprayed in a DC plasma torch (Plasmadyne SG-100, 40 kW subsonic plasma torch) which produced a 36 kilowatt Ar/He plasma jet. The powder injection was into the plasma tail flame. This resulted in the spheroidisation of all the zircon particles.

X-ray diffraction analysis of the powder on a Rigaku Geigerflex system equipped with a wide angle goniometer was used to determine the crystalline phases present. The X-ray diffraction analysis revealed that the zirconia was present in the tetragonal form of zirconia. The silica produced from the dissociation of the zircon during the plasma treatment was amorphous (glassy).

The powder was then heat treated in a Rapid High Temperature Furnace (Kanthal) at 1400° C. for 2 hours in order to coarsen the spinodal structure to such an extent that the tetragonal zirconia would transform to the thermodynamically stable monoclinic form on cooling. X-ray diffraction was used to confirm this. In order to prevent reduction in mechanical strength of the particles due to the phase transformation a very slow cooling rate was used through 720° C., the transformation temperature.

The silica was removed from the powder by leaching with a 60% aqueous solution of NaOH at 160° C. in a nickel crucible.

The powders were then examined under the SEM to check the morphology of the particles and also to obtain a particle size distribution.

Powder sizing—The spheroidised powders were mixed with water and then separated into narrow size ranges using a Warman Cyclosizing-apparatus. This consists of a series of five cyclones, the size ranges trapped in each cyclone depending on the operating parameters as well as the particle size and shape.

Particle size analysis—Particle size analysis was carried out by the direct measurement of SEM photographs of the particles using a Zeiss Particle Size Analyser TGZ-3.

Scanning Electron Microscopy (SEM)—A JEOL JSM-840 scanning electron microscope equipped with energy dispersive X-ray analysis facilities was used to examine the particles. Both secondary electron images and back scattered electron images were obtained. The latter gave atomic number contrast.

A typical pore structure of a zirconia particle made by the above method is shown in FIG. 1.

EXAMPLE 2

Two types of ceramic particles based on zirconia were used in the comparison of this example. One (referred to as PDZ later in this example) was prepared in the Department of Materials Engineering at Monash University in accordance with the methods of the present invention. These particles had an average size of 7 $\mu$m, a pore size of 1000 Å and a specific surface area of between 1.0 and 4.2 m$^2$/g (measured by BET). The other particles were provided by the 3M company, St. Paul, Minn. 55144, USA, (Batch-No. 90 588 P15) and were made in accordance with a different process (i.e. the precipitation process) to that of the present invention for use as a comparison to the PDZ materials. These particles had an average particle size of 15 $\mu$m a pore size of 160A and a surface area of 32 m$^2$/g.

Determination of the Surface Area by Adsorption of Phosphate

Phosphate anions are known to bind strongly to zirconia surfaces. Therefore, the amount of bound phosphate ions on the support particles can be used to determine the surface area of this support or after modification to determine the remaining uncovered surface of the particles.

These measurements were used as an alternative to elemental analysis to determine the success of the modification process of the present invention.

For this purpose a phosphate solution of known phosphate concentration was prepared. A part of this solution was stored as a standard solution for the determination of the concentration. To the other part zirconia particles were added and the suspension was shaken over night. Then the solid parts were removed by filtration and the phosphate concentration of the supernatant was measured.

EXAMPLE 3

Hydrothermal treatment to increase the hydroxyl group density on the zirconia surface To increase the hydroxyl group density on zirconia surfaces the hydrothermal treatment as previously described was able to achieve a higher amount of-reactive hydroxyl groups for the modification.

The zirconia particles were treated in an autoclave in a water steam atmosphere at 150° C. for different times reaching from 1 to 16 hours. After the treatment the particles were modified with a $C_{18}$-silane and the uncovered zirconia surface was determined by the adsorption of phosphate ions. One possible set of conditions to achieve optimal results was 6 hours at 150° C.

EXAMPLE 4

Molybdenum Blue Method

Orthophosphate and molybdate ions form an acidic solution of molybdophosphoric acid, which can be selectively reduced by hydrazine sulphate to form molybdenum blue, a compound of uncertain composition. This complex can be measured photometrically at its absorption maximum at 820–830 mn.

Procedure: The concentration of the sample should be smaller than 4 mg phosphorus per litre. 50 $\mu$l of sample at neutral pH was mixed with 10 $\mu$l molybdate solution and 4 $\mu$l hydrazine sulphate solution and diluted to 100 $\mu$l. The mixture was heated in a boiling water bath for 10 minutes and then cooled rapidly. The volume was adjusted and the absorption was measured at 690 nm. The absorption of the sample was measured in a microtiter plate together with different dilutions of the standard phosphate solution as calibration.

Table I shows the results of the phosphate adsorption on different modified and non-modified support materials. From the values obtained in Table I it can be readily seen that the amount of phosphate adsorbed on PDZ zirconia was considerable less than the amount adsorbed on the zirconia for both unmodified and modified forms of the respective zirconia. This indicates that the hydrothermal treatment of the zirconia significantly improves the ligand density during the modification step. Furthermore, the performance of the zirconia particles made in accordance with the present invention performed significantly better than the 3M derived particles due, it is thought, to the different structure of the pores of the particles made in accordance with the present invention which structure only clearly distinguishes the PDZ particles of the present invention.

Modification of the supports

Two principally different methods to modify the surface of a sorbent particle are available. The first approach is to use a silane which will react with a hydroxyl group present on the support surface. This will lead to a monomeric modification. The other possibility to introduce a desired interactive surface is to cover the surface of the particle with a polymer coating. The polymeric coating can but does not have to be covalently attached to the surface.

EXAMPLE 5

Modification with Mercantosilane and Cibacron Blue F3GA

Figure 2:
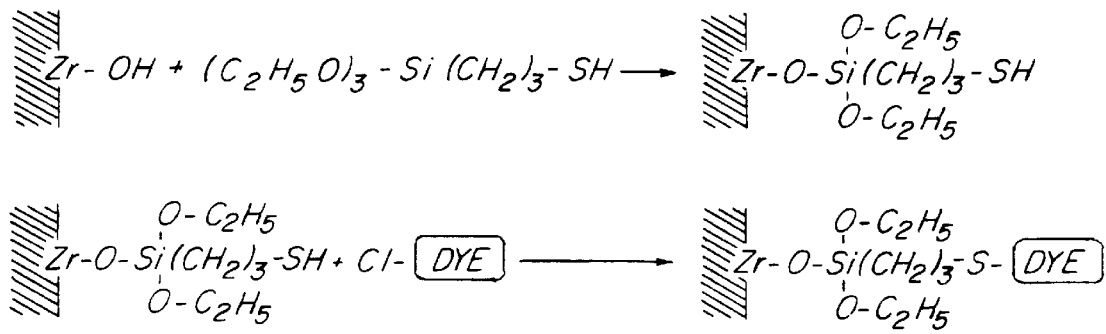
FIG. 2 is a modification of zirconia with Cibacron Blue F3GA.

To study the possibility to derivatise the zirconia particles a Cibacron Blue modification was chosen because it is easy to see whether the modification was successful or not by observation of the intensity of colour of the final product as shown in FIG. 2.

The modification with Cibacron Blue was performed in three steps. First a hydrothermal treatment, as described above (150° C., 6 hours) was performed to insure a high and uniform hydroxyl group distribution on the zirconia surface. Second the zirconia particles were activated with 3-mercaptopropyl-trimethoxysilane and then modified with Cibacron Blue F3GA. To couple the silane to the surface of the particles, the particles were suspended in nitric acid at a pH of 3.5. The silane was added and the suspension was shaken at 90° C. for three hours. The binding of the triazine dye was performed at 60° C. in sodium carbonate buffer at a pH of 8.0 containing 0.5M NaCl overnight.

The amount of silane necessary to modify the particles was calculated by the product of the specific surface area, the amount of zirconia, the hydroxyl group density (about 8 $\mu mol/m^2$) and the molecular weight of the silane. Because of steric reasons only half of the hydroxyl groups are accessible for the silane. Therefore, using 8 $\mu mol/m^2$ as hydroxyl group density results in a twofold excess of silane. A higher amount of silane should be avoided because of the tendency of the trimethoxy group to polymerise which may fill up some pores then rendering the particles less useful in subsequent applications.

Immobilising the dye is not limited by the number of reactive sites on the particles' surface but by the size of the molecule. The maximum amount of dye able to bind to the support is about 1 $\mu mol/m^2$. Again, a twofold excess was used for the reaction. After the reaction was completed the supports were washed with water and 2-propanol.

EXAMPLE 6

Modification with Octadecyldimethyl-chlorosilane

Figure 3:
FIG. 3 is a modification of zirconia with octadecylsilane.

First a hydrothermal treatment, as described above (150° C., 6 hours) was performed to insure a high and uniform hydroxyl group distribution on the zirconia surface. The ceramic support materials were modified with octadecyldimethyl-chlorosilane (ODS) in order to achieve RP-sorbents. The modification was performed in anhydrous toluene, using imidazole as a catalyst. The toluene was stored over sodium metal and freshly distilled before use. To remove physically adsorbed water from the surface of the particles the particles were suspended in the solvent, the imidazole and the silane were added and the mixture treated an an ultrasonic bath for five minutes and then heated under reflux for six hours. The silane was added in an eightfold excess assuming that the maximum ligand density is about 4 $\mu mol/m^2$ as shown in FIG. 3.

To prevent a grinding of the particles the use of a magnetic stirrer was avoided. After the reaction was finished, the sorbent material was washed with toluene, 2-propanol and water.

EXAMPLE 7

Modification with Polybutadiene

Another method of producing a reversed phase material in accordance with the present invention is to attach a polymeric layer onto the surface. Depending on the amount of polymer desired to bind on the surface different methods to prepare these support materials are available. The polymeric layer should not be too thick otherwise it will fill up the pores and decrease the surface area to a very high degree thus reducing the effectiveness of the particles. Pretreatment of the particles to increase the hydroxyl group surface concentration was not necessary in all cases for the coating with polybutadiene, but could be used if desired or required.

The particles were modified using two different amounts of prepolymerised polybutadiene (PBD) resulting in supports with different thickness of the polymeric layer. For the low carbon loading, the amount of PBD was calculated to be 0.5 mg/m$^2$. The PBD and the dicumylperoxide (DCP) were dissolved in dry pentane and the dried zirconia particles made in accordance with the method of the present invention were added. The pentane was removed under vacuum and the coated particles were heated to 60° C. under vacuum for 12 hours. The final step was a heat treatment at 200° C. under nitrogen atmosphere for 4 hours to crosslink the coating. To effect modification with the polybutadiene it is preferred that the particles have a large pore size.

EXAMPLE 8

Modification with Aminosilane and Carbohydrate

The purpose of this Example was to produce a hydrophilic bonded phase which would be easy to derivatise and which would have a high pH stability. Glucose and Maltose were coupled to aminopropyl derivatised PDZ-powder. First a hydrothermal treatment, as described above (150° C., 6 hours) was performed to insure a high and uniform hydroxyl group distribution on the zirconia surface. To 1 g of zirconia (dried overnight under vacuum at 180° C.) suspended in 50 ml anhydrous toluene an amount of 3-aminopropyltrimethoxysilane was added corresponding to a twofold excess compared to the accessible hydroxyl group density on the zirconia surface (as described in Example 5 for the modification with 3-mercaptopropyl triethoxysilane). The reaction was performed by treating the suspension under reflux for six hours. After completion the particles were extensively washed with toluene, 2-propanol, 10 mM HCl and water.

Glucose or maltose was coupled to the aminopropyl zirconia in a 50 mM sodium carbonate buffer pH 6.8. An estimated 10 times excess of glucose or maltose was used for the coupling, which was performed by shaking the suspension at 60° C. overnight. An equimolar amount compared to the amount of carbohydrate of sodiumcyanoborohydride was included to reduce the Schiff's base that is formed. After the reaction was completed the particles were washed and suspended in acetone to crosslink different amounts of butadiene diepoxide reaching from 10 to 100 μl per gram of particles have been used. The crosslinking reaction was performed for two hours at ambient temperature with borontrifluoride diethyletherate as catalyst.

Figure 4:
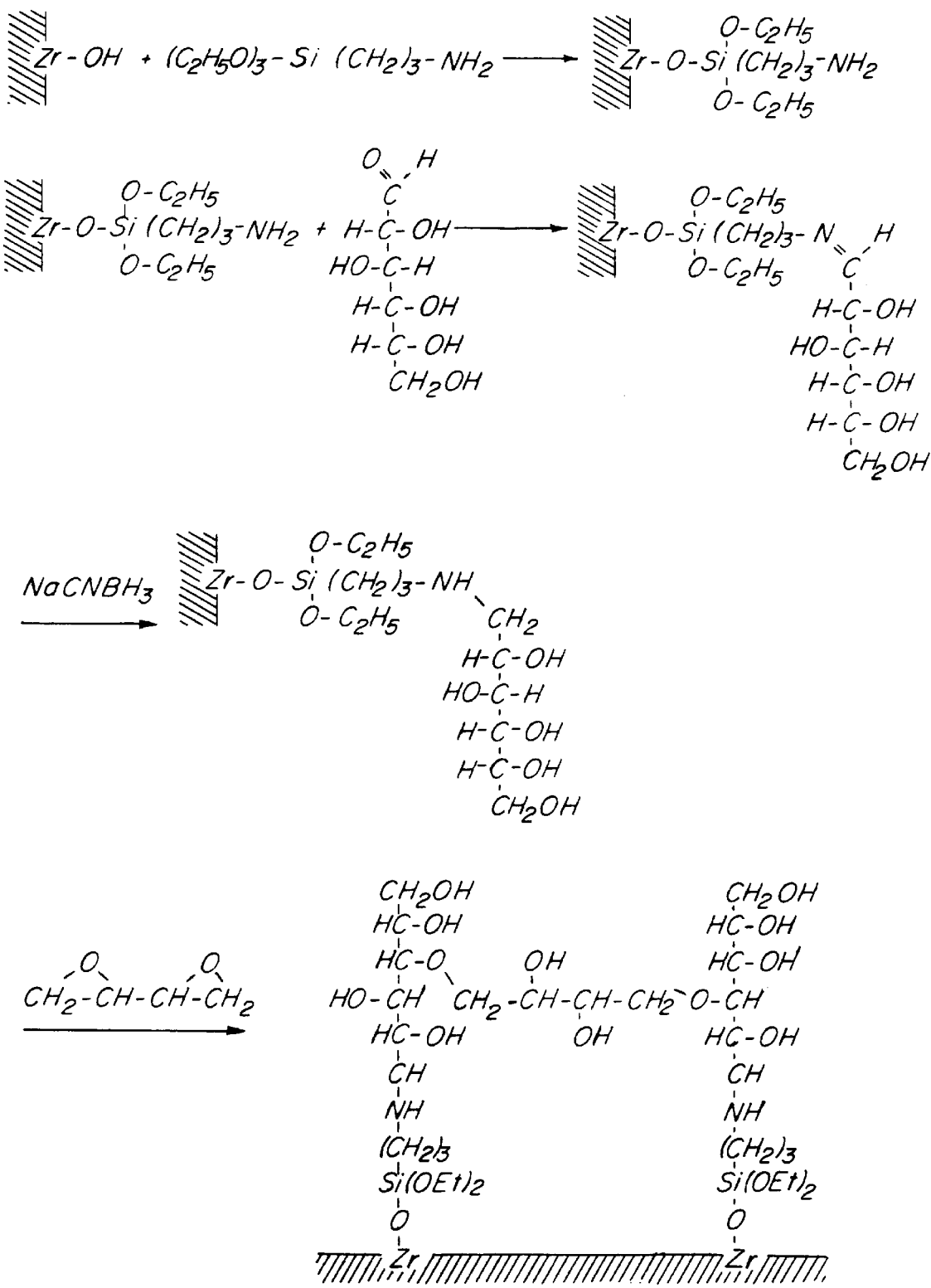
FIG. 4 is a modification and crosslinking of zirconia with carbohydrates.

Any remaining epoxide rings were opened either by an acid treatment or by deactivation with ethanolamine. The derivatised sorbents were either used without any further treatment or modified with Cibacron Blue F3GA. For the modification the particles were suspended in 100 mM Sodium carbonate buffer pH 9.5 containing 0.5M NaCl and an excessive amount of Cibacron Blue was dissolved. The reaction was performed at 60° C. overnight, after which the particles were washed with water and 2-propanol to give the results in FIG. 4. The amount of coupled aminosilane was determined by elemental analysis and coupled glucose via the difference between noncoupled glucose in the supernatant and glucose in the "coupling solution". The result indicates that 97% of the amino groups are derivatised by a glucose unit. This is supported by the fact that zirconia modified via aminosilane and glucose does not give any colour reaction with picryl sulphonic acid, a reagent detecting amino group.

Modification with 3-glycidoxypropyl-trimethoxysilane (Glymo)

Two different modification procedures were used; modification at anhydrous conditions and modifications in aqueous solution at acidic conditions. Under anhydrous conditions the silane will bind monomerically to the zirconia while at acidic conditions a polymeric layer will be formed.

EXAMPLE 9

Modification under Anhydrous Conditions

Two grams of zirconia were rehydroxylated with hydrothermal treatment as described in Example 3 at 150° C. for six hours, after which the particles were dried under vacuum at 180° C. overnight. The particles were suspended in 50 ml anhydrous toluene. 17 mg silane and 15 mg imidazole as a catalyst were added and the suspension was treated under reflux for six hours. The modified particles were washed with toluene, 2-propanol and water.

EXAMPLE 10

Modification under Aqueous Conditions at Acidic pH

The zirconia particles were rehydroxylated as described under Example 3. Two grams zirconia were suspended in 20 ml of a 10% solution of Glymo in water adjusted at pH 3.5 with nitric acid. The suspension was treated at 90° C. for two hours after which the particles were washed with water to neutrality.

pH Stability Tests

The stability of the various modified particles made in accordance with the methods of the present invention were investigated in three different ways. Firstly, the modified particles were treated with buffers of various pH and the leakage was directly monitored in a UV detector; secondly radioactively labelled ligands were immobilised and the leakage was detected by release of radioactivity in the supernatant; and thirdly the performance of the particles in HPLC column experiments was used as an indicator of ligand leakage.

1) direct monitoring of ligand leakage in batch experiment:

The Cibacron Blue modified particles were suspended in 100 mM sodium carbonate buffer solutions at different pH-values and shaken overnight. After this time the particles were centrifuged and the supernatant was examined for leaking ligands. This was done photometrically at 280 nm. In one experimental series several different buffers were employed for a pH stability test of glucose and Cibacron Blue modified zirconia. The buffers used were sodium phosphate, sodium carbonate and β-alanine all at concentrations of 100 mM, as well as water titrated with sodium hydroxide.

2) Detection of $^{14}C$ labelled ligands in batch experiments 100 mg of modified zirconia particles were suspended in 2 ml of a 0.1 m sodium carbonate buffer and shaken for 24 hours. After this time two samples (each 0.5 ml) were taken and mixed with 4.5 ml scintillation liquid and counted for 2 min. The particles were resuspended in a new buffer with increased pH. The pH was increased in steps of 0.5 and the whole procedure was repeated up to pH 14.

3) RP chromatographic performance as indicator of ligand leakage.

The octadecyl modified support was packed in a column supplied by Bischoff, Leonberg FRG. The column dimensions were 33 mm in length×8 mm ID (column volume 1.66 ml). The HPLC equipment used consisted of two Waters pumps Model 6000A, a Waters gradient former Model 660, a Millipore Waters LC spectrometer Lambda Max Model 481, a Waters Data Module and a DuPont Chartrecorder.

Sample: Aniline, Toluene and Naphthalene (1 mg/ml each)
Solvent: Water+0.1% Trifluoroacetic acid (TFA)
Flowrate: 1 ml/min
Wavelength: 254 nm The column was exposed to a 0.1M carbonate buffer of pH 9.0 for 1000 column volumes with a flow rate of 1.0 ml/min. After each 100 column volumes the performance was tested by injecting the test mixture. After 1000 column volumes the pH was increased by one. A decrease in retention time or in the plate number would have indicated a decrease in ligand coverage.

No change in the retention time could be observed up to pH 13.

Detection of "Non-Specific" Protein interaction on Carbohydrates and Glymo derivatised Zirconia Sorbents Four different modified zirconia materials were tested: particles modified with glucose, maltose, and also glymo prepared under anhydrous and aqueous conditions. The sorbents were packed in 100×2 mm analytical columns and equilibrated in the chromatographic buffer. Three different solvents were used. 10 mM sodium carbonate buffer pH 6.5 with no, 100 and 500 mM NaCl added. Three proteins were used as adsorbate: bovine ribonuclease A (pI 8.9), bovine carbonic anhydrase (pI 5.9) and ovalbumin (pI 4.7). The proteins were run three times each at all salt concentrations. The total volume was determined with acetone. The elutions of these proteins were expressed in terms of elution volume of the protein divided by the elution volume of the acetone. Since a material with 3000A pore size was used, there should be no exclusion effect and the proteins should elute at the same volume as the acetone unless interactions between the protein and the particle surface occur.

pH Stability Tests in a Batch Experiment

EXAMPLE 11

Using Dye Modified Zirconia

To determine the chemical stability of the modification the zirconia modified with Cibacron Blue F3GA was suspended n buffer solutions of various pH and then shaken for 24 hours. After this treatment the suspension was centrifuged and the supernatant was examined for dye bleeding off the support. When no leakage occurred the whole procedure was repeated in a buffer adjusted at a pH 0.5 higher than the previous. Under these conditions no leakage occurred at pH 8.0, 8.5, 9.0 and 9.5. At pH=10.0 the supernatant was coloured, indicating that the modification is not stable under these conditions.

The water in the supernatant was evaporated and the solid remaining was used for an elemental analysis. The material was tested for its nitrogen, silicon and zirconium content. According to the presumed structure, the cleavage could occur at three different places:

1. the bead was actually dissolving, which would give positive results in the zirconium silicon and nitrogen content,
2. the cleavage occurred between the particle surface and the silicon, giving positive results for the silicon and nitrogen content but negative results for the zirconium and
3. the cleavage occurred at the sulfur group between the silane and the dye molecule, resulting in very small amounts of both silicon and zirconium.

The actual result of the elemental analysis was 8.8% nitrogen, 1.3% silicon and 0.0047% zirconium, indicating that the cleavage occurred at the Zr-O-Si bond.

EXAMPLE 12 pH Stability Tests using the Carbohydrate-Dye Modified Zirconia

A stability test for zirconia was performed using different buffers: a phosphate, a carbonate and a β-alanine buffer. Water titrated with NaOH was used as a reference. The stability tests were performed with a carbohydrate-Cibacron Blue modified zirconia in a batch experiment. Loss of the modification was monitored at 280 nm. In each case 450 mg zirconia particles were suspended in 5 ml buffer and shaken for 24 hours each. The experiments were started at pH 9.0 and the pH was increased by 1 after each run. The results of this experiment are presented in Table 2.

This experiment showed that there were no significant differences in stability of this bonded phase in the different buffer solutions, indicating that these ions are not able to displace covalently attached silanes from the zirconia surface. The modification in this case showed a high stability, at least up to pH 11.0. The experiments were repeated several times, always with the same result.

The modified zirconia produced with immobilised maltose were stable up to pH 12 as documented in Table 2.

EXAMPLE 13

In this example two materials were compared, one with crosslinking and one without crosslinking. Both materials were zirconia particles made in accordance with the methods of the present invention and derivatised with Cibacron Blue F3GA. A 100 mM phosphate buffer was used. The results obtained are set out in Table 3.

These results show clearly that not only the crosslinked material but also the non-crosslinked particles are remarkably stable. The high stability of these modified zirconia supports were also seen, when glucose-dye modified particles were suspended in 1M sodium hydroxide and treated for 24 hours. After washing to neutrality and drying no leakage of the dye could be detected. It is needless to point out that the zirconia particles made in accordance with the present invention show a substantially higher stability compared to silica particles.

EXAMPLE 14

The results from the "non-specific" protein interaction measurements are presented in Table 4. The results for the carbohydrate modified zirconias, both glucose and maltose, were very similar, so only the results for the glucose modified particles are listed in this Table.

The three different modified sorbents showed distinctly different properties. The Glymo support prepared in water at an acidic pH has a polymeric coating, which is covalently attached to the surface. This coating results in a good coverage of the surface indicated by the protein elution characteristics of the support. However, this kind of modification leads to a thick layer reducing the chromatographic performance of the support due to increased pore diffusion effects. Both the carbohydrate modified particles and the support synthesised with Glymo under anhydrous conditions result in a monomeric modification with a controlled thickness of the interactive surface.

From these monomeric modified supports, the particles with the carbohydrate ligands showed a superior performance over the particles modified with Glymo. It is thought that this difference could be explained by the length of the carbohydrate ligand exceeding that of Glymo and therefore preventing the protein from reaching the zirconia surface. There is also a qualitative difference between these two materials. While the carbohydrate modified sorbent interacted only with the most basic protein (Ribonuclease A), the Glymo modified particles also adsorbed the more acidic proteins ovalbumin and carbonic anhydrase. This indicates, that there are both Lewis acid and base groups present on the zirconia surface.

The results of the experiments indicated in the foregoing examples of this specification demonstrate an easy method of producing chromatographic sorbent materials having superior chemical stability when compared to silica based sorbents and having, better physical characteristics than sorbents based on organic polymers.

Modification with Iminodiacetic Acid (IDA)

In the following examples the synthesis of a metal chelate and conconavalin-A modified sorbents and their evaluation are described. To modify the zirconia support with IDA the following procedure was used. In a first step the silane is produced. 1 g iminodiacetic acid and 1.503 g NaOH are dissolved in 18 ml water and cooled in an ice bath. 1.776 g 3-glycidoxypropyltrimethoxy-silane is added dropwise. The solution is stirred and allowed to warm to room temperature and then heated to 60° C. overnight.

Figure 5:
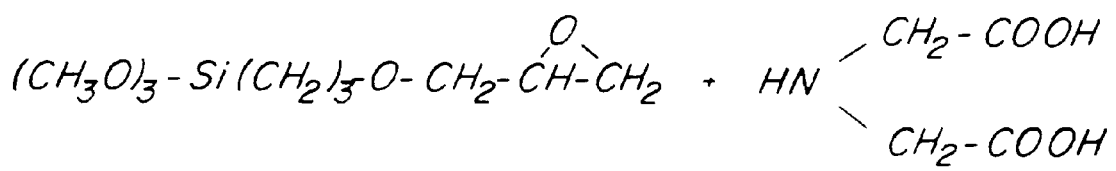
FIG. 5 is a modification of zirconia with aminoacetic acid.
Figure 5:
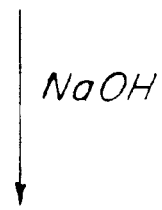
Figure 5:
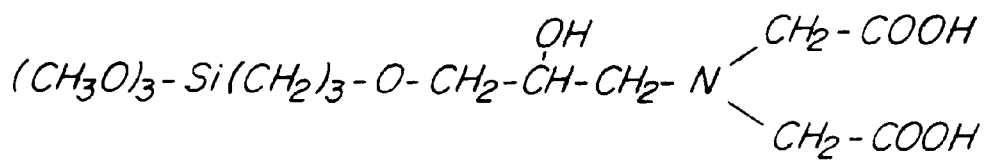
Figure 5:
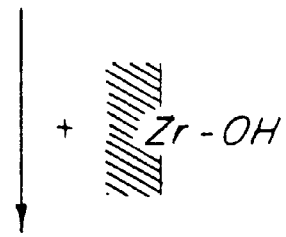
Figure 5:
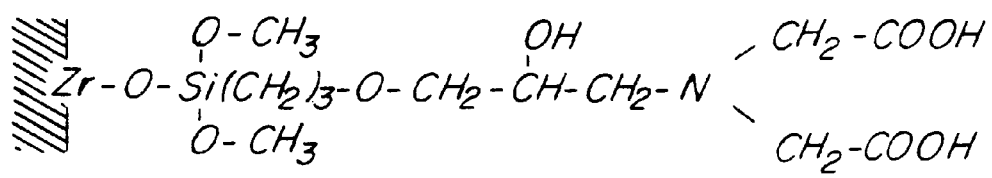

To modify the zirconia particles after first subjecting the particles to a hydrothermal treatment, as described above (150° C., 6 hours) to insure a high and uniform hydroxyl group distribution on the zirconia surface, a five times excessive amount of the silane solution is adjusted to pH 3.0 with HCl and 1 g of particles is suspended in this solution. The suspension is heated to 90° C. for three hours giving the results in FIG. 5.

The particles were washed with 0.1M hydrochloric acid, water and 2-propanol and suspended in a solution of coppersulphate to saturate the chelate groups with Cu(II) ions.

EXAMPLE 13

Modification with Concanavalin-A

The modification with a protein is done in two steps. First a hydrothermal treatment, as described above (150° C., 6 hours) was performed to insure a high and uniform hydroxyl group distribution on the zirconia surface. Secondly the support material is modified with 3-isothiocyanatopropyl-triethoxysilane to introduce reactive groups onto the zirconia surface and then the protein is attached via free amino groups on the protein surface.

To modify the support with the silane, the particles were dried at 180° C. in vacuum. Toluene was dried over sodium metal and freshly distilled. The particles were suspended in the toluene and the silane was added. The amount of silane was calculated for 8 $\mu$mol/m$^2$ support surface area. A small amount of imidazole was added as a catalyst. The suspension was sonicated for five minutes to remove air trapped inside the pores. The mixture was treated under reflux for 24 hours and then washed with toluene, 2-propanol and water.

Figure 6:
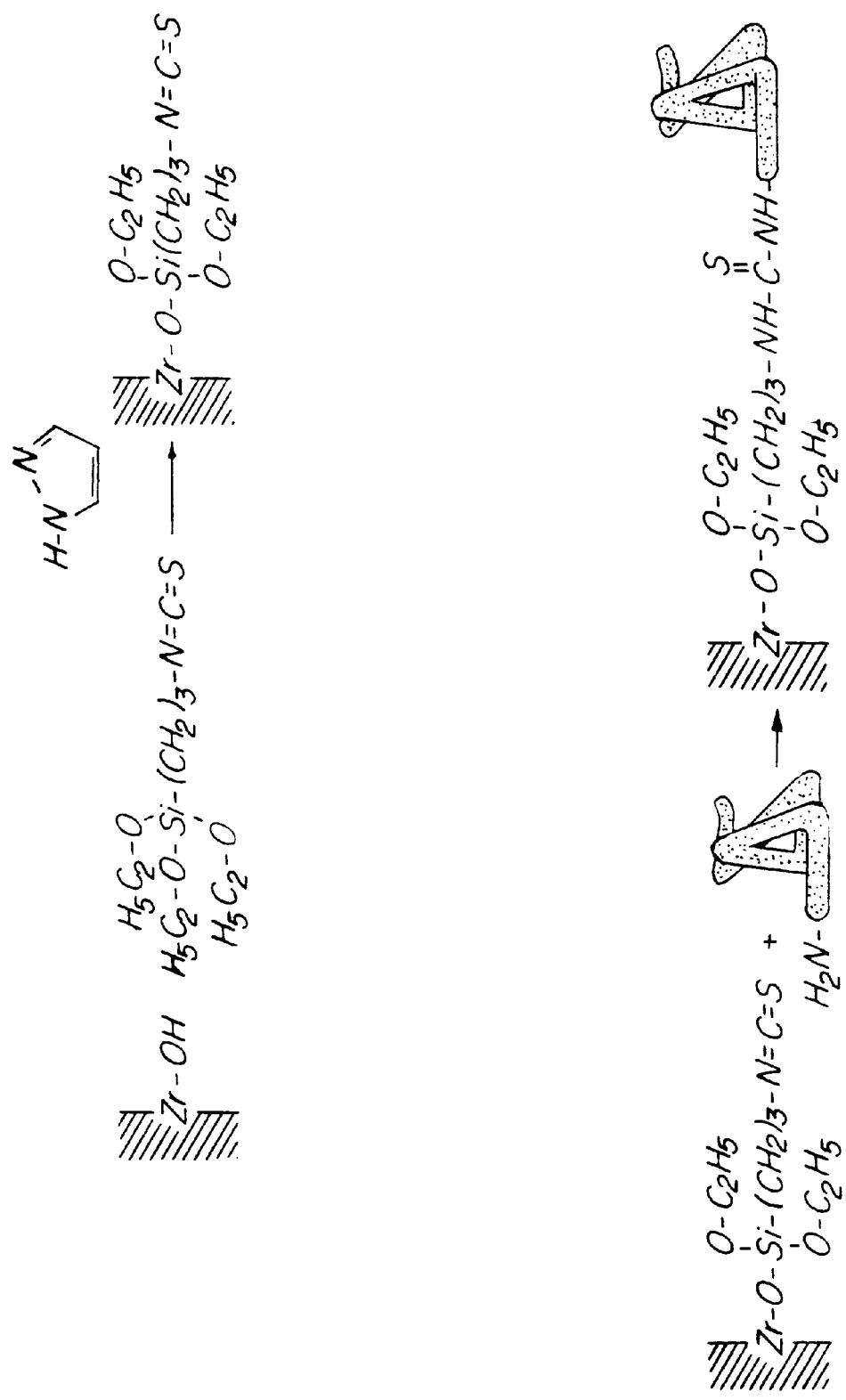
FIG. 6 is a modification of zirconia with a protein such as Concanavalin-A, pepsin, papain, trypsin, chymotrypsin.
Figure 7:
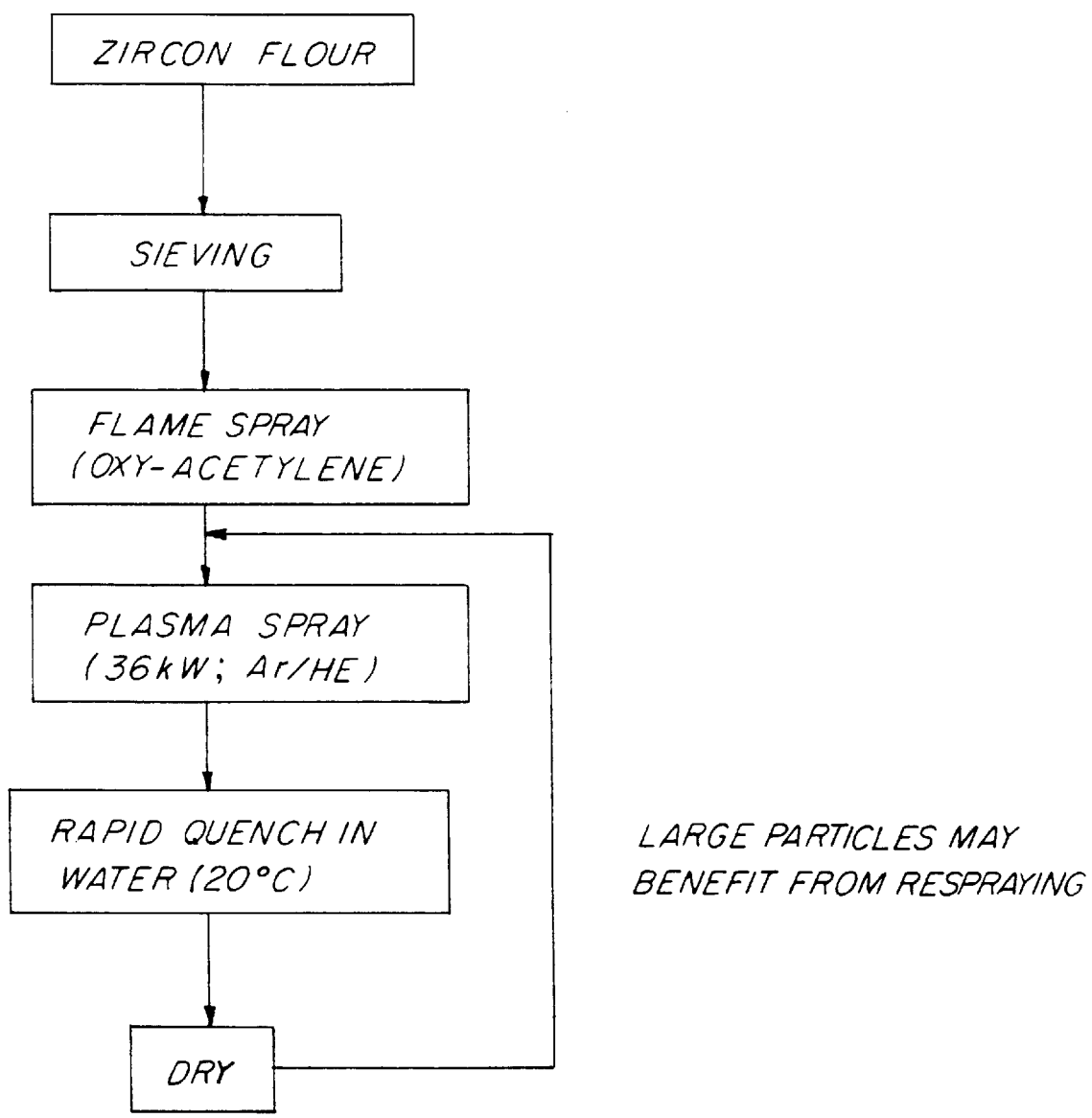
FIG. 7 and FIG. 8 are flow charts of the steps of typical examples of making the particles in accordance with the present invention showing typical processing conditions. It is to be noted that not all particles are made by a method involving all of the steps shown.
Figure 8:
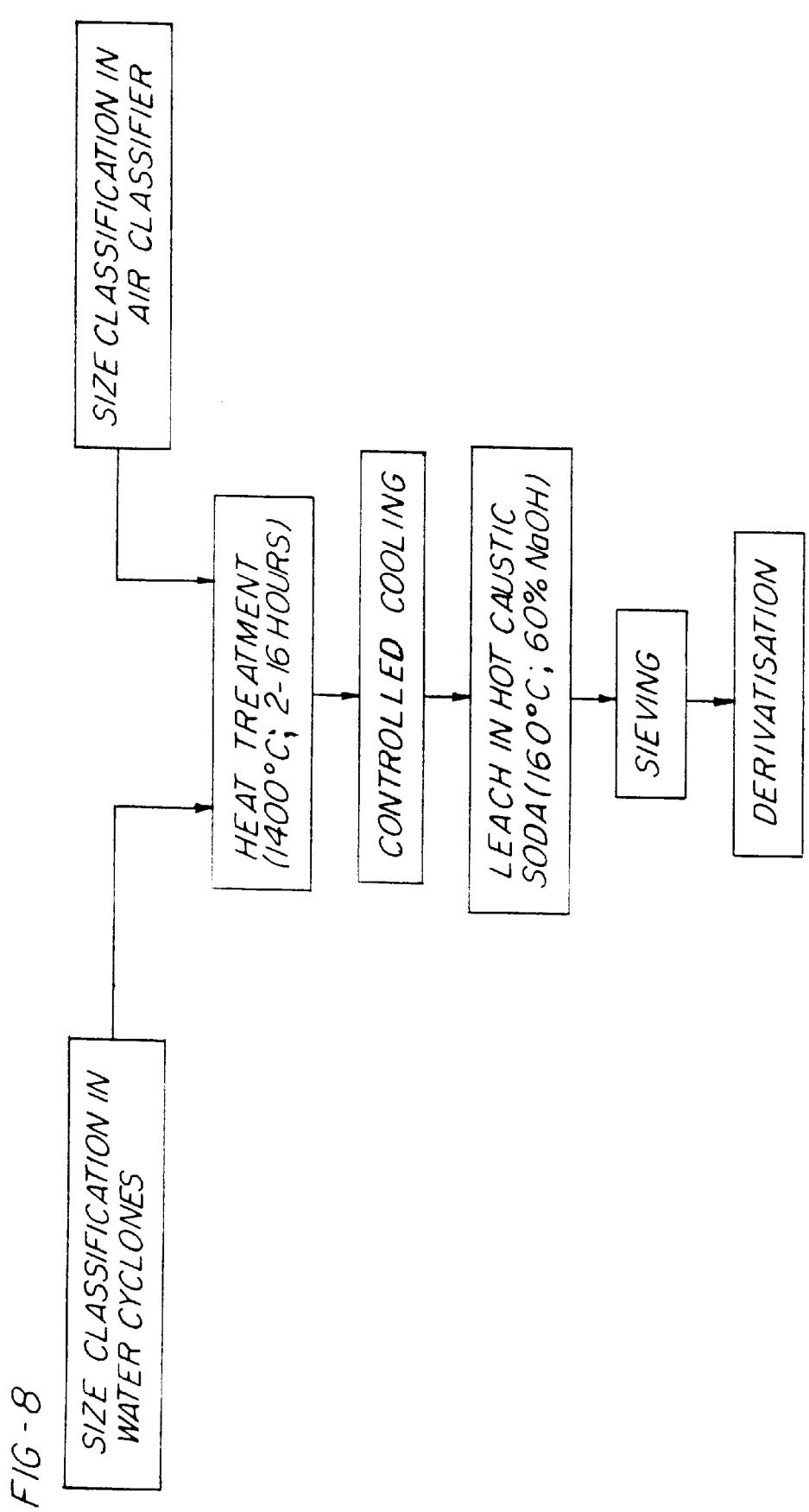

To attach the protein, the modified particles were suspended in acetate buffer pH 6.5 and 10 mM $MnCl_2$ and $CaCl_2$ were added to maintain the biological activity of Con-A. The suspension was treated at room temperature for 48 hours and washed with the same buffer. The particles were never dried. The results are shown in FIG. 6.

To block remaining NCS-groups the particles were treated with a solution of ethanolamine pH 7.0 overnight.

EXAMPLE 14

Batch Adsorption Experiments with Metal Chelate Modified Zirconia 1 g of 3M zirconia was suspended in 20 ml of 20 mM phosphate buffer pH 7.0 with 0.2M NaCl added. Due to the lower specific surface area of the PDZ particles 2 g were used for the adsorption experiments with this support material. Horse heart myoglobin was dissolved in the same buffer used for the suspension at a concentration of 1 mg/ml and added successively to metal chelate sorbents. During the whole experiment the temperature of the suspension was kept at 7° C. The rate of adsorption was monitored at 280 mn and recorded until equilibrium was reached. The equilibrium concentrations were used to plot the adsorption isotherm which was evaluated using three different linearisation approaches (double reciprocal plot, semi reciprocal plot and Scatchard plot [5–10].

EXAMPLE 15

Batch Adsorption Experiments with Concanavalin-A Modified Zirconia

For the adsorption of horseradish peroxidase on Concanavalin-A modified zirconia a 20 mM phosphate buffer with 0.2M NaCl added was adjusted to pH 6.5. The buffer contained 1 mM of each $CaCl_2$, $MnCl_2$ and $MgCl_2$ to sustain the biological activity of Concanavalin-A. The buffer was filtered prior to use to remove undissolved Mn- or Ca-phosphate precipitation. As before either 1 g of 3M zirconia or 2 g of PDZ zirconia was used in each experiment. The particles were suspended in 25 ml of the buffer and the suspension was thermostatted at 7° C. Horseradish peroxidase was dissolved in the described buffer at a concentration of 1 mg/ml. To examine whether the binding was due to specific interaction the adsorbate was eluted after the recording of the adsorption isotherm was completed using methyl-D-mannopyranoside and the adsorption step was repeated.

To evaluate the adsorption data the same approach as in case of the metal chelate modified supports was employed. In both cases the adsorption coefficient of the protein under the chosen conditions was determined by recording a calibration curve without the presence of sorbent material. The results for Qm and Kd are listed in Table 5. The utilisation of the 3M zirconia for the Con-A affinity adsorption appeared to be not practical due to a significant reduction of the pore size by the ligand and a resulting very restricted pore diffusion of the adsorbate. The result of the pore diffusion appears when the adsorption kinetics for the adsorption of myoglobin on IDA-zirconia is compared with the adsorption of peroxidase onto Con-A modified particles. An increase in temperature to 25° C. in order to increase the diffusion kinetics did not improve the results in a satisfying way, so only the results obtained with the PDt zirconia at 7° C. are presented. The results for Qm and Kd are listed in Table; 6.

The good concordance between the first adsorption and the consecutive experiment after specific elution indicates that the binding of peroxidase to the sorbent is due to specific interactions between the carbohydrate binding site of Concanavalin-A and the glyco-part of the peroxidase molecule and that the elution step is complete to retain the original capacity.

The results obtained in the foregoing examples of this specification show clearly that the modification chemistry for various sorbents can also be applied to synthesise affinity supports. The zirconia particles of the present invention can be surface modified in a variety of ways in accordance with diverse chemical separation applications that the surface modified particles are to be used in.

EXAMPLE 16

Desirable properties of support material for immobilisation of enzymes are: hydrophilic surface characteristics, good packing properties, high surface area, permeability and mechanical stability.

Two inorganic, porous sorbent materials were used as a matrix to attach the proteases. The main focus was put on a porous zirconia. Due to the high density of zirconia, these particles offer ideal characteristics for use in bioseparators. They exhibit a superior settling rate in closed systems and allow higher flowrates in continuous reactors.

For the immobilisation of the protease the particles of zirconia were activated with 3-isothiocyanatopropyl-triethoxysilane as described in Example 13.

Coupling of the enzyme to the activated carrier. 200 mg activated support were suspended in 10 ml buffer solution containing 11 mg protease. The suspension was shaken headover at room temperature for 24 hours. After the coupling procedure, the suspension was filtered and the supernatant preserved. The immobilised enzyme was washed with 0.5M NaCl and the remaining NCS-groups were blocked with ethanolamine.

The coupling procedure were modified in order to accommodate the specific requirements of each enzyme. For pepsin lower pH values were used since pepsin is rapidly and irreversibly denaturated at alkaline pH values, but is stable between pH 5 and 5.5; the presence of calcium chloride in the coupling mixture for trypsin improves the specific activity of the immobilised trypsin by reducing the autodigestion. The application of buffers which contain amino groups have been avoided during the coupling process to avoid blocking of the NCS groups by these buffers.

The following coupling conditions were applied for the different proteases:

Trypsin:
    a) 0.02M $CaCl_2$-solution, pH 7.0
    b) 100 mM HEPES buffer with 0.02M $CaCl_2$, pH 8.0
    c) 199 mM Clark and Lubs solution (according to Elliot et al) with 0.02M $CaCl_2$, pH 9.0

Chymotrypsin:
   a) 0.02M $CaCl_2$ solution, pH 7.0
   b) 100 mM HEPES, pH 8.0
Papain:
   a) water, pH 7.0
   b) 100 mM HEPES buffer, pH 8.0
   c) 100 mM Clark and Lubs solution, pH 9.0 (only with zirconia)
Pepsin:
   a) 100 mM Citrate buffer, pH 5.0
   b) 100 mM Citrate buffer, pH 5.5
   c) 100 mM Citrate buffer, pH 6.0
   d) 100 mM Acetate buffer, pH 4.5
   e) 100 mM Acetate buffer, pH 5.6
a), b) and c) were performed with silica only.

After the coupling and blocking of remaining NCS groups the enzyme derivatives were washed extensively with buffer and stored at room temperature in the following buffers:

Trypsin: in 100 mM Tris/HCl, 20 mM $CaCl_2$, pH 8.0
Chymotrypsin: in 100 mM Tris/HCl, pH 8.0
Papain: in 100 mM Acetate buffer, pH 5.0
Pepsin: in 50 mM Acetate buffer, pH 4.0

EXAMPLE 17

Humic substances appear in all open water sources, and their removal is an important task to improve the water quality. Although humic acid is not toxic per se it Gas a distinct brownish colour, making the water less attractive to the consumer. Because of the huge volumes involved, an effective water purification method has to be efficient, fast and inexpensive. A stirred tank or fluidised bed adsorption setup with dense, high capacity particles is preferred to the more costly alternatives, e.g. packed bed purification systems, because of the scale-up requirements (megalitres per hour requirements are often encountered in water process facilities) and the associated process economics. The particles act as ion exchangers, typically anionic exchangers.

A weak anionic exchanger (4-amino-4',4"-bisdimethylamino-triphenylcarbinol, 4-amino malachite green) was synthesised by condensing 1 part p-nitrobenzaldehyde with 2 parts N,N'-dimethylaniline. The nitrogroup was reduced to form an amine group, which also reduced the carbinol group. The carbinol group was reintroduced in a third step to form the target compound.

Zirconia was hydrothermally treated as described before and modified with 3-isothiocyanotopropyltriethoxysilane to introduce NCS-functional groups to the zirconia surface, which are able to react with the amine group of the 4-amino malachite green molecule.

For the preparation of the strong anionic exchangers, the zirconia (or silica) particles were modified with a polystyrene-based coating. The zirconia particles were hydrothermally treated as described previously and modified with 3-aminopropyltriethoxy-silane. Styrene was polymerised using anionic polymerisation, initiated with sodium naphthalene to achieve a narrow molecular weight range. The polymer was chloromethylated and coupled to the amino-modified zirconia or silica. An excessive amount of chloromethylated polystyrene was added ensuring that only a small portion of the chloromethyl groups of a given polystyrene chain had the chance to react with the activated zirconia, leaving the majority of the chloromethyl groups available for the generation of ion exchange groups as well as resulting in a tentacle type modification. The unreacted chloromethyl groups were derivatised with either trimethylamine or triethylamine resulting in a zirconia adsorbent chemically coated with polystyrene-trimethylammonium chloride or polystyrene-triethylammonium chloride groups.

To determine the effectiveness of using surface modified zirconia in removing humic acid from a river, water sample obtained from a river in the wine growing district of South Australia was obtained and different amounts of the modified zirconia adsorbents were suspended in 50 ml of the water sample under controlled temperature conditions and the adsorption process monitored continuously from the change in optical absorbance at 254 nm.

It was found that the humic acid substances in Barossa Valley water consist of a variety of compounds with different affinities for ion exchangers of different strength. Three different surface modification procedures resulted in adsorbents which exhibit different ion exchange capacities. A malachite green modification can be considered a weak anion exchanger while the triethyl- and trimethyl-phenylammonium-chloride modifications are strong ion exchangers. The trimethyl modification resulted in an even stronger ion exchanger than the triethyl modification. The various strengths of the ion exchangers dominate the way the adsorbents interact with the humic substances in the water. Besides the maximum capacity, the adsorption kinetics are also a very important feature in the adsorption process because they determine the throughput or the efficiency of the system. The best performances were observed when the malachite green and the trimethylphenylammonium modifications were used, whilst the triethylphenylammonium modified SAX particles showed significantly slower kinetics.

Due to the higher density of zirconia however, these particles should have a distinct advantage in terms of their settling rate when they are employed in large scale expanded bed processes. Faster settling rates mean faster separation times between the liquid and the solid phase and an increase in efficiency due to a reduced cycle time. Another important Advantage of surface modified zirconia adsorbents is the high chemical stability over a wide range of pH conditions, thus offering a greater variety of elution and regeneration possibilities.

Advantages and Industrial Applicability

The uniform distribution of pores in the porous zirconia particle render porous zirconia of the present invention particularly useful in applications relating to the separation of chemicals and biochemicals as well as for use as supports for catalysts and catalyst compositions.

The porous zirconia of the present invention is chemically stable and can be used in alkaline media in which porous silica fails. The porous zirconia has good strength and is of high density when compared to porous silica and organic polymers. The porous zirconia of the present invention may be used in the purification of high value chemicals, polymers and high molecular weight biochemicals using packed or fluidised beds of porous zirconia particles. The porous zirconia of the present invention may also be used for the analysis of high molecular weight polymers and biochemicals by chromatographic techniques using immobilised low molecular weight ligands bound to the surface of the porous zirconia. The porous zirconia of the present invention may also be used for the chromatographic analysis of chemicals and biochemicals using highly specific, bound, high molecular weight ligands or the like. other applications for the use of porous zirconia of the present invention include biosensors which may be used in on-line sensors for process and environmental control, as supports for bio-catalysts and as supports for conventional catalysts.

The porous zirconia of the present invention may also be used to separate contaminants. Such separation applications include the recovery of product from reaction mixtures. These include the recovery in the downstream processing of fermentation broths or cell cultures or as an alternative to ultrafiltration. The porous zirconia may be used as a sorbent for separation of micellar mixtures without liquid/liquid extractions. The porous zirconia may also be used for high resolution removal of toxins or contaminants from process streams or recovery of high value inorganic materials such as the rarer metals or the like. The porous zirconia may also be used for the removal of liquid aerosols from gas streams with, or without, recovery of the liquid phase.

The porous zirconia of the present invention which has been used in chromatographic, separative and catalysis applications and which has been spent may be readily regenerable by the burning of any organic matter out of the porous zirconia. This is particularly advantageous where the porous zirconia is used to extract organic molecules from process streams.

TABLE 1

| Material | amount of phosphate adsorbed [mg] | free surface area [%] |
|---|---|---|
| 3M not modified | 1.53 | 100 |
| 3M Cibacron Blue mod. | 0.39 | 25.5 |
| 3M Glucose modified | 0.67 | 43.8 |
| PDZ not modified | 0.158 | 100 |
| PDZ Cibacron Blue mod. | 0.036 | 22.8 |
| PDZ $C_{18}$ modified | 0.023 | 14.5 |

TABLE 2

| Buffer/pH | 9.0 | 10.0 | 11.0 | 12.0 | 13.0 |
|---|---|---|---|---|---|
| phosphate | 0.26 | 0.25 | 0.25 | 0.31 | 0.46 |
| β-alanine | 0.22 | 0.25 | 0.33 | 0.38 | 0.56 |
| carbonate | 0.25 | 0.32 | 0.34 | 0.36 | 0.56 |
| NaOH | 0.31 | 0.26 | 0.28 | 0.46 | 0.59 |

TABLE 3

| Support/pH | 9.0 | 10.0 | 11.0 | 12.0 | 13.0 | 14.0 |
|---|---|---|---|---|---|---|
| non crossl. | 0.027 | 0.031 | 0.031 | 0.037 | 0.077 | 0.081 |
| crosslinked | 0.025 | 0.032 | 0.029 | 0.029 | 0.054 | 0.076 |

TABLE 4

| | Protein | no salt | 100 mM NaCl | 500 mM NaCl |
|---|---|---|---|---|
| a | Ovalbumin | 0.97 | 1.05 | 1.18 |
| | Carbonic anhydrase | 1.07 | 1.07 | 1.05 |
| | Ribonuclease A | not eluted | 2.01 | 1.04 |
| b | Ovalbumin | not eluted | 1.09 | 0.99 |
| | Carbonic anhydrase | not eluted | not eluted | 1.32 |
| | Ribonuclease A | not eluted | 1.74 | 1.20 |
| c | Ovalbumin | 0.96 | 1.02 | 1.07 |
| | Carbonic anhydrase | 0.99 | 1.01 | 1.04 |
| | Ribonuclease A | not eluted | 1.27 | 1.13 |

Table 4: Protein interaction on different hydrophilic modified zirconia supports:
a Glucose modified particles
b Glymo modified under anhydrous conditions
c Glymo modified under acidic aqueous conditions
The elution of the proteins is expressed in elution volume of the protein divided by the elution volume of acetone

TABLE 5

| | double rec. plot | semi rec. plot | Scatchard plot |
|---|---|---|---|
| | 3M zirconia | | |
| all data used | $q_m = 3.68 \cdot 10^{-2}$ $K_d = 5.09 \cdot 10^{-4}$ | $q_m = 3.19 \cdot 10^{-5}$ $K_d = 2.83 \cdot 10^{-7}$ | $q_m = 3.58 \cdot 10^{-5}$ $K_d = 3.61 \cdot 10^{-7}$ |
| 5 smallest conc. neglected | $q_m = 3.53 \cdot 10^{-5}$ $K_d = 3.27 \cdot 10^{-7}$ | $q_m = 3.18 \cdot 10^{-5}$ $K_d = 2.49 \cdot 10^{-7}$ | $q_m = 3.34 \cdot 10^{-5}$ $K_d = 2.89 \cdot 10^{-7}$ |
| | PDZ zirconia | | |
| all data used | $q_m = 4.46 \cdot 10^{-6}$ $K_d = 4.65 \cdot 10^{-8}$ | $q_m = 7.67 \cdot 10^{-6}$ $K_d = 1.76 \cdot 10^{-7}$ | $q_m = 6.84 \cdot 10^{-6}$ $K_d = 1.16 \cdot 10^{-7}$ |
| spurious data points neglected | $q_m = 6.04 \cdot 10^{-6}$ $K_d = 1.12 \cdot 10^{-7}$ | $q_m = 7.75 \cdot 10^{-6}$ $K_d = 2.12 \cdot 10^{-7}$ | $q_m = 7.00 \cdot 10^{-6}$ $K_d = 1.55 \cdot 10^{-7}$ |

TABLE 6

| | double rec. plot | semi rec. plot | Scatchard plot |
|---|---|---|---|
| PDZ zirconia modified with Con-A: first adsorption experiment | | | |
| all data used | $q_m = 1.76 \cdot 10^{-5}$ $K_d = 5.16 \cdot 10^{-6}$ | $q_m = 5.65 \cdot 10^{-6}$ $K_d = 1.48 \cdot 10^{-6}$ | $q_m = 5.54 \cdot 10^{-6}$ $K_d = 1.42 \cdot 10^{-6}$ |
| smallest conc. neglected | $q_m = 4.66 \cdot 10^{-6}$ $K_d = 1.08 \cdot 10^{-6}$ | $q_m = 5.59 \cdot 10^{-6}$ $K_d = 1.43 \cdot 10^{-6}$ | $q_m = 5.39 \cdot 10^{-6}$ $K_d = 1.33 \cdot 10^{-6}$ |
| second adsorption after elution with α-methylmannose | | | |
| all data used | $q_m = 1.32 \cdot 10^{-5}$ $K_d = 6.35 \cdot 10^{-6}$ | $q_m = 4.92 \cdot 10^{-6}$ $K_d = 1.97 \cdot 10^{-6}$ | $q_m = 6.31 \cdot 10^{-6}$ $K_d = 2.70 \cdot 10^{-6}$ |

We claim:
1. A method for the production of porous zirconia comprising the following steps in sequence:
   (a) heating a zirconia-silica composition to provide particles of said composition in a substantially homogeneous liquid melt form;
   (b) quenching said particles to effect spinodal decomposition of the liquid melt to provide quenched particles comprising a silica-rich phase and a zirconia-rich phase, wherein said zirconia-rich phase comprises zirconia substantially in a tetragonal form;
   (c) annealing said quenched particles to transform the tetragonal form of the zirconia rich phase to the monoclinic form on cooling so as to provide annealed particles comprising a continuous monoclinic zirconia-rich phase and a continuous silica-rich phase;
   (d) leaching said silica-rich phase from the annealed particles to provide porous monoclinic zirconia particles each of said particles comprising a three dimensionally continuous interpenetrating network of interconnected pores, said pores being of substantially constant diameter throughout their length.
2. A method according to claim 1 in which a third phase is formed in step (c).
3. A method according to claim 2 in which the third phase is zircon.
4. A method according to claim 3 in which the zircon is not leached away from and remains in the zirconia phase after leaching when the silica phase is leached away.
5. A method according to claim 4 in which the porous zirconia particles comprise zirconia and zircon in which the zircon is intimately incorporated into the zirconia.
6. A method according to claim 1 in which the zirconia-silica composition is a substantially uniform composition or provides a liquid melt of a substantially uniform composition.

7. A method according to claim 1 in which the zirconia-silica composition is an admixture of zirconia or zirconia-containing material and a silica or silica-containing material or a compound containing both zirconia and silica or a composition, mixture or compound which decomposes to provide a substantially homogeneous liquid melt of zirconia and silica.

8. A method according to claim 7 in which the molar ratio of zirconia to silica is about 1:1.

9. A method according to claim 1 in which the percentage of zirconia to silica in the quenched particles is from about 100-1% molar zirconia to 0–99% molar silica.

10. A method according to claim 1 in which the zirconia-silica composition is zircon.

11. A method according to claim 1 in which the zirconia-silica composition is in the form of a powder or particles.

12. A method according to claim 1 in which the pore size of a single zirconia particle is substantially constant and there is a distribution of varying pore sizes between the particles, such as a distribution of 0.01 to 0.2 $\mu$m for pore size in a distribution of particle size range of 40 to 80 $\mu$m.

13. A method according to claim 1 in which the zirconia-silica composition forms the liquid melt at temperatures in excess of about 2400° C.

14. A method according to claim 1 in which heating of the zirconia-silica composition occurs in a plasma arc torch or similar.

15. A method according to claim 1 in which the particles of zircon heated in the plasma arc torch have a particle size in the range of from 5 to 100 $\mu$m.

16. A method according to claim 1 in which the zircon particles are elongated and on heating the particles first dissociate and then melt to form a substantially homogeneous liquid melt.

17. A method according to claim 1 in which the zirconia-silica composition is heated by flame spraying using an oxyacetylene flame.

18. A method according to claim 17 in which the zirconia-silica particles are heated by flame spraying with an oxyacetylene flame and the particle sizes so treated are in the range of from 3 to 15 $\mu$m.

19. A method according to claim 1 in which the particles of the substantially homogeneous liquid melt are quenched at a cooling rate sufficient to prevent nucleation and growth of zirconia spherulites and to allow spinodal decomposition of the liquid melt into a substantially fine micro-structure of zirconia-rich and silica-rich phases, optionally containing a further phase.

20. A method according to claim 1 in which the quenched particles have wave lengths of about 100 Å and have uniform periodicity and three dimensional continuity.

21. A method according to claim 1 in which homogeneous liquid melt is quenched in a liquid.

22. A method according to claim 1 in which quenching provides a cooling rate in the range of about $10^5$ to $10^{7°}$ C. $\text{sec}^{-1}$.

23. A method according to claim 1 in which the quenched particles comprise both a zirconia-rich and silica-rich phase in which the zirconia-rich phase is substantially in tetragonal form.

24. A method according to claim 1 further comprising additional leaching of the silica-rich phase so that the zirconia-rich phase will transform from tetragonal to stable monoclinic form.

25. A method according to claim 1 in which the annealing takes place below a temperature at which there is substantially no recombination of zirconia and silica.

26. A method according to claim 25 in which some recombination of zirconia and silica occurs to form zircon to enhance the strength of the porous particles produced by leaching the silica therefrom, said zircon being optionally incorporated into the zirconia phase.

27. A method according to claim 1 in which annealing takes place at a temperature in the range from about 1000° C. to 1400° C., over a period 5 hours.

28. The method of claim 1 in which the transformation temperature of dissociated zircon quenched and subsequently annealed is about 720° C.

29. A method according to claim 1 in which the transformation of the tetragonal form to the monoclinic form does not lead to substantial shattering of the annealed particles on cooling.

30. A method according to claim 1 in which alkali or hydrofluoric acid are used to leach the silica-rich phase.

31. The method of claim 30 in which the annealed particles are leached with alkali, at a temperature of about 160° C.

32. A porous zirconia particle or composition made accordance with the method of claim 1.

33. A porous zirconia particle produced by the method recited in claim 5.

34. A porous zirconia particle produced by the method recited in claim 6.

35. A porous zirconia particle produced by the method recited in claim 24.

36. A method for the production of porous tetragonal zirconia comprising the following steps in sequence:
   (a) heating a zirconia-silica composition to provide particles of said composition in the form of a substantially homogeneous liquid melt;
   (b) quenching said particles such that spinodal decomposition of the liquid melt occurs to provide quenched particles comprising a silica-rich phase and a zirconia-rich phase;
   (c) annealing said quenched particles to coarsen the zirconia-rich phase such that the desired pore size can be obtained in step (d);
   (d) leaching said silica-rich phase from the annealed particles to provide porous tetragonal zirconia particles comprised of three dimensionally continuous interpenetrating networks of pores, said pores being of substantially constant diameter throughout their length.

37. The method of claim 36 in which the tetragonal zirconia is stabilised by the addition of dopants of rare earth oxides or other metal oxides, or combinations thereof.

38. The method of claim 36 in which the zirconia-silica composition further comprises a dopant intimately incorporated into the composition.

39. The method of claim 38 in which the dopant is yttria.

40. The method of claim 36 in which the particles in said step (b) comprise a third phase of a dopant of ytrria, the yttria being incorporated into the zirconia-rich phase.

41. The method of claim 40 in which the dopant is calcia, or magnesia.

42. A porous zirconia particle or composition made accordance with the method of claim 36.

43. A porous zirconia particle produced by the method recited in claim 37.

44. A method for the production of porous cubic zirconia comprising the following steps in sequence:
   (a) heating a zirconia-silica composition to provide particles of said composition in the form of a substantially homogeneous liquid melt;

(b) quenching said particles to effect spinodal decomposition of the liquid melt to provide quenched particles comprising a silica-rich phase and a zirconia-rich phase;

(c) annealing said quenched particles to coarsen the zirconia-rich phase such that desired pore size can be obtained in step (d);

(d) leaching said silica-rich phase from the annealed particles to provide porous cubic zirconia particles comprised of three dimensionally continuous interpenetrating networks of interconnected pores, said pores being of substantially constant diameter throughout their length.

45. A method according to claim 44 in which the particles in step a further in step a comprise a dopant.

46. A method according to claim 44 in which the zirconia-silica composition further comprises a dopant intimately incorporated into the zirconia-silica composition.

47. The method of claim 44 in which the particles in said step (b) comprise a third phase of a dopant.

48. A porous zirconia particle produced by the method recited in claim 44.

49. A porous zirconia particle produced by the method recited in claim 45.

* * * * *